United States Patent [19]

Utz et al.

[11] Patent Number: 5,194,442

[45] Date of Patent: Mar. 16, 1993

[54] 2,3,4,5-TETRAHYDRO-1-BENZOXEPINS, THE USE THEREOF AND PHARMACEUTICAL PRODUCTS BASED ON THESE COMPOUNDS

[75] Inventors: Roland Utz, Messel; Heinrich C. Englert, Hofheim am Taunus; Bernward Schölkens; Erik Klaus, both of Kelkheim, all of Fed. Rep. of Germany

[73] Assignee: Hoechst Aktiengesellschaft, Frankfurt am Main, Fed. Rep. of Germany

[21] Appl. No.: 606,132

[22] Filed: Oct. 31, 1990

Related U.S. Application Data

[63] Continuation of Ser. No. 407,618, Sep. 15, 1989, abandoned.

[30] Foreign Application Priority Data

Sep. 17, 1988 [DE] Fed. Rep. of Germany ....... 3831697

[51] Int. Cl.$^5$ .................. A61K 31/44; C07D 405/04
[52] U.S. Cl. .................... 514/337; 514/422; 546/269; 548/525
[58] Field of Search ............ 546/269; 548/525; 514/337, 422

[56] References Cited

U.S. PATENT DOCUMENTS

4,446,113  5/1984  Evans et al. ............ 548/525
4,555,509  11/1985 Evans et al. ............ 548/525

OTHER PUBLICATIONS

Goodman and Gilman's The Pharmacological Basis of Therapeutics pp. 191, 623, 785, 926.

Primary Examiner—Jane T. Fan
Attorney, Agent, or Firm—Finnegan, Henderson, Farabow, Garrett and Dunner

[57] ABSTRACT

2,3,4,5-Tetrahydro-1-benzoxepins of the formula I

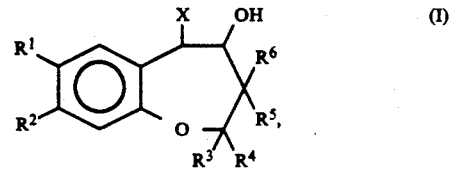

with $R^1$ equaling, inter alia, H, alkyl, alkoxy, Hal, alkylsulfonyl, arylsulfonyl, $R^2$ equaling H, alkyl, alkoxy, OH, $R^3$ to $R^6$ H or alkyl and X equaling

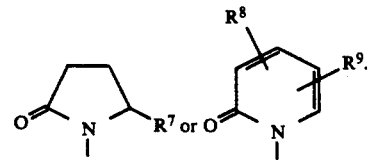

have excellent efficacy as antihypertensives, as coronary therapeutics, as agents for the treatment of cardiac insufficiency, of disturbances of cerebral and peripheral blood flow or of disturbances of intestinal motility, premature labor, obstructions of the airways or of the urinary tract or of the biliary tract or as spasmolytics.

10 Claims, No Drawings

2,3,4,5-TETRAHYDRO-1-BENZOXEPINS, THE USE THEREOF AND PHARMACEUTICAL PRODUCTS BASED ON THESE COMPOUNDS

This is a continuation of application Ser. No. 07/407,618 filed Sep. 15, 1989, and now abandoned.

The invention relates to 2,3,4,5-tetrahydro-1-benzoxepins of the formula I

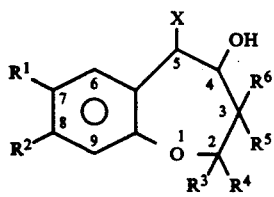

in which
$R^1$ represents H, $(C_1-C_4)$-alkyl, OH, $(C_1-C_4)$-alkoxy, halogen, CN, $NO_2$, CO-$(C_1-C_4)$-alkyl,

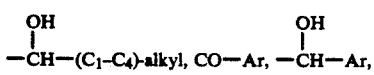

COOH, carboxy-$(C_1-C_4)$-alkyl, $(C_1-C_4)$-alkyl-$SO_r-$ or $ArSO_r-$, where r represents 0, 1 or 2 and Ar represents an aromatic or heteroaromatic system which is unsubstituted or substituted by 1 to 3 identical or different $(C_1-C_4)$-alkyl, $(C_1-C_4)$-alkoxy, halogen, CN or $NO_2$ radicals,
$R^2$ represents H, OH, $(C_1-C_4)$-alkoxy or $(C_1-C_4)$-alkyl,
$R^3$, $R^4$, $R^5$ and $R^6$ are identical or different and represent H or $(C_1-C_4)$-alkyl, and
X has the meaning of α) or β),

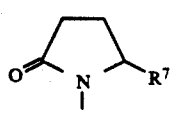  α)

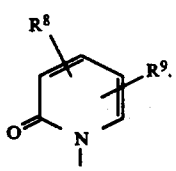  β)

where $R^7$ is H or methyl, $R^8$ and $R^9$ are identical or different and represent H, $(C_1-C_2)$-alkyl, halogen, nitro or CN.

An aromatic system Ar means phenyl, naphthyl or biphenylyl, and a heteroaromatic system Ar is a radical of a 5-or 6-membered O-, N- and/or S-heterocyclic ring, especially furyl, thienyl, isothiazolyl, oxazolyl, isoxazolyl, pyrazolyl, imidazolyl, thiazolyl, pyridyl, pyrazinyl, pyrimidinyl, pyridazinyl and triazinyl.

Halogen means F, Cl, Br or I, preferably F and Cl.

The carbon atoms 4 and 5 of the 2,3,4,5-tetrahydro-1-benzoxepin system of the formula I are asymmetrically substituted. In this connection, the invention relates only to those compounds which have opposite configurations at these centers, that is to say have a "trans" orientation of the substituents on these carbon atoms. If the substituents $R^1$, $R^2$, $R^3$, $R^4$, $R^5$, $R^6$ and X contain centers of asymmetry, or if $R^3/R^4$ and/or $R^5/R^6$ are not the same (and thus generate one or two asymmetric carbon atoms), the invention includes compounds with centers with both the S and R configuration.

The compounds can be in the form of optical isomers, of diastereomers, of racemates or of mixtures thereof.

Preferred compounds of the formula I are those in which $R^1$ represents H, halogen, CN, nitro, phenylsulfinyl, phenylsulfonyl and benzoyl, with the phenyl radicals in the abovementioned meaning being substituted, and $R^2$, $R^3$, $R^4$, $R^5$, $R^6$ and X being as defined above.

Additionally preferred are compounds of the formula I in which $R^1$ represents H, halogen, CN, nitro, phenylsulfinyl, phenylsulfonyl and benzoyl, with the phenyl radicals being unsubstituted or substituted by 1 to 2 identical or different halogen atoms, $R^2$ denotes H, and $R^3$, $R^4$, $R^5$, $R^6$ and X are as defined above.

Also preferred are compounds of the formula I in which $R^1$ represents H, CN, nitro, phenylsulfinyl, phenylsulfonyl and benzoyl, with the phenyl radicals being unsubstituted or substituted by 1 to 2 identical or different halogen atoms, $R^2$, $R^3$, $R^4$, $R^5$ and $R^6$ represent a hydrogen atom and X has the meaning of β with $R^8$ and $R^9$ assuming the definitions mentioned in the introduction.

Very particularly preferred compounds of the formula I are those in which $R^1$ represents H, CN, nitro, phenylsulfinyl, phenylsulfonyl and benzoyl, with the phenyl radicals being unsubstituted or substituted by one halogen atom, $R^2$, $R^3$, $R^4$, $R^5$ and $R^6$ represent a hydrogen atom and X has the meaning of α with $R^7$ being as defined above.

No similar compounds have hitherto been disclosed; EP-A 0,277,612, 0,277,611 and 0,273,262 disclose chroman systems.

A new class of substances with valuable pharmacological properties has now been found in the form of the compounds I.

Animal experimental investigations show that they are suitable for the treatment of disorders of the cardiovascular system, for example for the treatment of hypertension, of cardiac insufficiency or of disturbances of blood flow in the coronary system such as, for example, angina. Disturbances of cerebral and peripheral blood flow are likewise influenced beneficially. Furthermore, compounds I are able to influence smooth-muscle organs such as uterus, bronchi, intestines and biliary system, the urinary tract (ureter, bladder and urethra) in the sense of spasmolysis. They are therefore also suitable for the treatment of diseases associated with spasms of these organs, for example for the treatment of premature labor in pregnancy, of ureteral or biliary colic, of obstructive airway diseases such as asthma, of distrubances of intestinal motility such as, for example, of irritable colon or of bladder incontinence.

The invention additionally relates to a process for the preparation of the compound I, which comprises
a) reacting compounds of the formula II

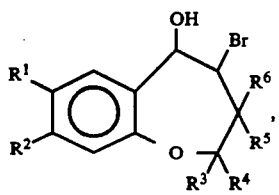

in which R¹ to R⁶ are as defined above, with compounds of the formula III or IV

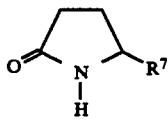

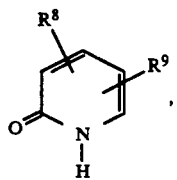

or
b) reacting compounds of the formula V

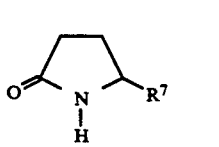

in which R¹ to R⁶ are as defined above, with compounds of the formula III or IV

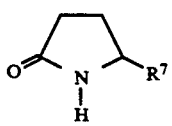

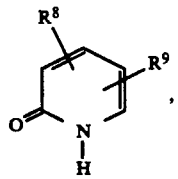

or
c) reacting compounds of the formula II

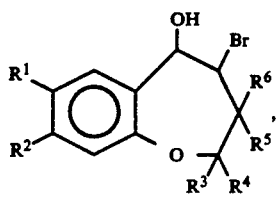

in which R¹ to R⁶ are as defined above, with compounds of the formula VI and VII

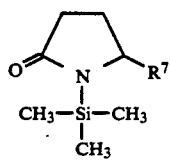

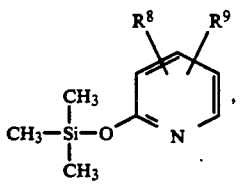

or
d) reacting compounds of the formula V

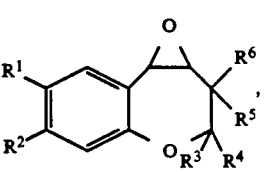

in which R¹ to R⁶ are as defined above, with compounds of the formula VI and VII

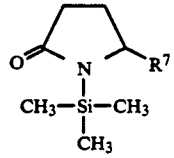

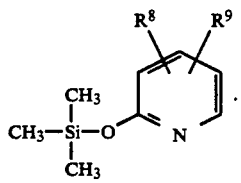

When the compounds I are prepared by methods a) or b) this is carried out by reacting the compounds II or V in a suitable solvent such as, for example, dimethyl sulfoxide, dimethylformamide, tetrahydrofuran or N-alkylated ureas, for example, 1,3-dimethyltetrahydro-2(1H)-pyrimidinone (DMPU), with the compounds III or IV, preferably with the action of strong bases such as, for example, sodium hydride, potassium hydride, lithium diisopropylamide, lithium bis-(trimethylsilyl)-amide, potassium bis-(trimethylsilyl)-amide or similar bases known to be suitable for lactam N-alkylations. The temperature for this reaction can be varied within wide limits, it is preferably between 0° C. and room temperature or at temperatures which can be slightly above room temperature.

Compounds which can be prepared only with difficulty by methods a) or b) can be obtained by process c) or d). In this case, the compounds II or V are stirred together with the compounds VI or VII in the presence of catalytic or molar amounts of a desilylating agent such as potassium tert.-butylate or tetrabutylammonium fluoride trihydrate in a dipolar aprotic solvent such as THF and the like. It is also possible to carry out the reaction without addition of a solvent in the presence of an excess of the liquid compounds VI or VII. The temperature for this can vary within wide limits.

Thus, the compounds I according to the invention are obtained even at room temperature in many cases, but only after heating to 60°–80° C. in other cases. In fact, in a few cases even higher temperatures are necessary.

A very advantageous procedure for the reactions by method d) comprises suspending compounds of the formula V in an excess of the liquid compounds from VI or VII and adding catalytic amounts of tetrabutylammonium fluoride trihydrate, the initial products being compounds of the formula Ia

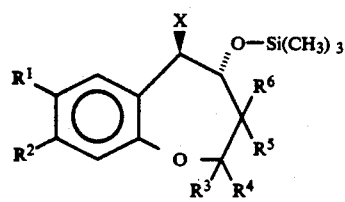

which, as intermediates which can easily be purified, can be converted with molar amounts of tetrabutylammonium fluoride trihydrate in THF into the compounds I according to the invention.

Compounds of the formula III and V can in many cases be bought or can be synthesized straightforwardly by methods known from the literature.

The silyl compounds of the formula VI and VII can be prepared in a manner known per se from compounds of the formula III and IV, for example by heating with 1,1,1,3,3,3-hexamethyldisilazane and subsequent distillation.

The compounds of the formula II and V are mostly new and can be obtained as described hereinafter.

Starting from suitably substituted 4-phenoxybutyric acids of the formula VIII it is possible to prepare the corresponding carbonyl chlorides of the formula IX which can be cyclized smoothly in a manner known per se in the presence of aluminum trichloride in 1,2-dichloroethane to give 2,3-dihydro-1-benzoxepin-5(4H)-ones of the formula X.

Alternatively, in a few cases the cyclization is also achieved by heating the carboxylic acids of the formula VIII in polyphosphoric acid.

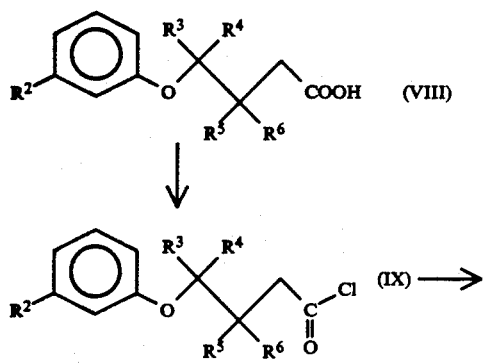

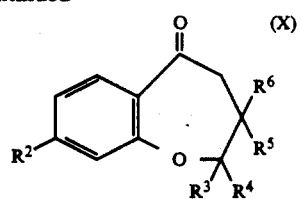

The ketones of the formula X can be converted in a manner known per se into the alcohols of the formula XI. Particularly well suited for this purpose is, for example, NaBH$_4$ in methanol or ethanol.

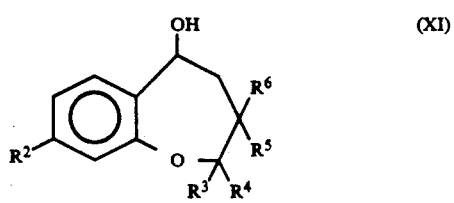

The introduction of the substituents R$^1$ with the meanings defined above can be carried out from case to case either on compounds of the formula X or XI. Thus, for example, it is possible for the 2,3-dihydro-1-benzoxepin-5(4H)-ones of the formula X to be smoothly nitrated in concentrated sulfuric acid by addition of solid sodium nitrate at 0° C. to give compounds of the formula XII.

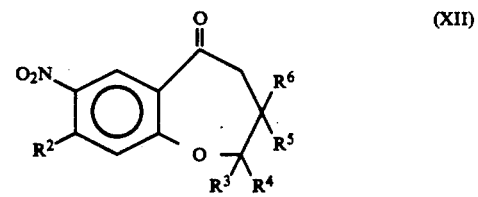

The introduction of a bromine atom in the 7 position of the 2,3,4,5-tetrahydrobenzoxepin system is achieved by reacting the compounds of the formula XI with N-bromosuccinimide in glacial acetic acid at 10°–20° C. Compounds of the formula XIII are obtained in this way.

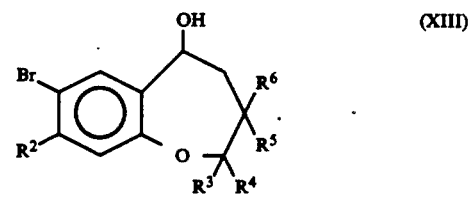

The compounds of the formula XIII eliminate, on addition of catalytic amounts of p-toluenesulfonic acid in toluene at the boiling point, water which can be removed by azeotropic distillation. It is possible in this way to prepare compounds of the formula XIV.

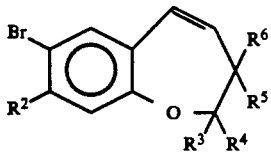
(XIV)

The compounds of the formula XIV can be metalated in the 7 position with the aid of 2 equivalents of tert.-butyllithium in THF at −78° C. Obtained in this way are aryllithium compounds of the formula XV which can be reacted in a manner known per se with a large number of electrophiles to give compounds of the formula XVI.

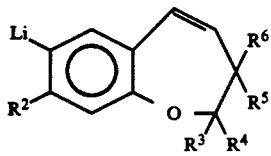
(XV)

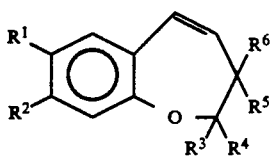
(XVI)

For example, reaction of compounds of the formula XV with diaryl disulfides results in compounds of the formula XVII

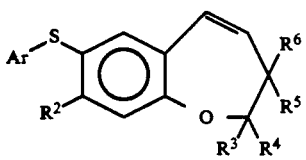
(XVII)

it being possible for Ar in the abovementioned meaning to be substituted.

The compounds of the formula XVII can be converted selectively in a manner known per se into sulfoxides and sulfones of the formula XIX and XVIII respectively, for example by oxidation with hydrogen peroxide in glacial acetic acid.

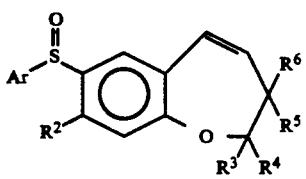
(XIX)

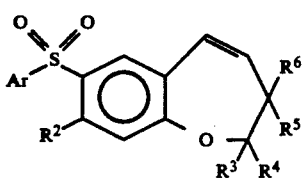
(XVIII)

The aryllithium compounds of the formula XV can, inter alia, also be reacted with alkyl halides, preferably with iodides, aldehydes, amides, carbonic acid derivatives, carbon dioxide and halogens. It is possible in this way often to introduce the substituents $R^1$ defined above into the compounds of the formula XIV in one reaction step, or application of standard organic reactions results, as shown above by way of example, in the desired substituents $R^1$ in position 7.

It is also possible to introduce numerous substituents $R^1$ starting from compounds of the formula XIII. For this purpose, compounds of the formula XIII are metalated with 3 equivalents of tert.butyllithium in THF at −90° C. to give the dilithium compounds of the formula XX,

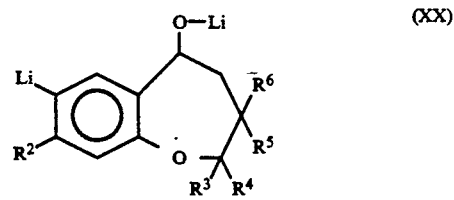
(XX)

which, as shown above by way of example on compound XV, can be converted in a manner known per se into compounds of the formula XXI.

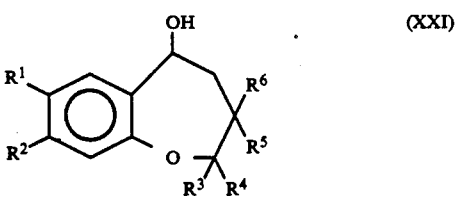
(XXI)

The elimination of water is carried out on compounds of the formula XXI to give compounds of the formula XVI as described above.

The compounds of the formula XVI can be reacted in a manner known per se with N-bromosuccinimide in aqueous dimethyl sulfoxide to give compounds of the formula II.

Epoxides of the formula V can be obtained in a manner known per se from bromohydrins of the formula II, for example by the action of bases on compounds of the formula II.

Enantiomerically pure final products I can be obtained from racemic final products I by conventional methods of racemate resolution, such as, for example, separation by chromatography using chiral phases or derivatization of the racemic products with optically pure acid derivatives or with optically pure isocyanates. The diastereoisomeric isocyanates or esters obtained thereby can be separated by conventional methods (crystallization or chromatography) and converted into the optically pure final compounds I by elimination of the optically active auxiliary group on the 4-OH group. Separation of the diastereomeric 4-menthoxyacetates has proven particularly advantageous in this connection.

As already mentioned, the compounds I according to the invention can be used as antihypertensives, as coronary therapeutics, as agents for the treatment of cardiac insufficiency, of disturbances of cerebral and peripheral blood flow or of disturbances of intestinal motility, premature labor, obstructions of the airways or of the urinary tract or of the biliary tract or as spasmolytics.

In this connection, pharmaceuticals which contain the compound I can be administered orally, parenterally, intravenously, rectally or by inhalation, with the preferred form of administration being dependent on the disease which is to be treated. The compounds I can, moreover, be used alone or together with pharmaceutical auxiliaries, specifically both in veterinary and in human medicine.

The particular auxiliaries suitable for the desired pharmaceutical formulation are familiar to those skilled in the art on the basis of their expert knowledge. Besides solvents, gel-formers, suppository bases, tablet auxiliaries and other active substance vehicles, it is possible to use, for example, antioxidants, dispersing agents, emulsifiers, antifoam agents, flavorings, preservatives, stabilizers or colorants.

For a form for oral use, the active compounds are mixed with the additives suitable for this purpose, such as excipients, stabilizers or inert diluents, and converted by customary methods into suitable dosage forms such as tablets, coated tablets, hard gelatin capsules, aqueous, alcoholic or oily suspensions, or aqueous, alcoholic or oily solutions. Examples of inert vehicles which can be used are gum arabic, magnesia, magnesium carbonate, potassium phosphate, lactose, glucose or starch, especially corn starch. This preparation can be carried out both as dry and as wet granules. Examples of suitable oily excipients or solvents are vegetable or animal oils, such as sunflower oil or fish liver oil.

For subcutaneous or intravenous administration, the active compounds are converted into solution, suspension or emulsion, if desired with the substances customary for these purposes, such as solubilizers, emulsifiers or other auxiliaries. Examples of suitable solvents are water, physiological saline solution or alcohols, for example, ethanol, propanol, glycerol, as well as sugar solutions such as glucose or mannitol solutions or else a mixture of the various solvents mentioned.

Examples of pharmaceutical formulations suitable for administration in the form of aerosols or sprays are solutions, suspensions or emulsions of the active substance of the formula I in a pharmaceutically acceptable solvent such as, in particular, ethanol or water, or a mixture of such solvents. The formulation can, if required, also contain other pharmaceutical auxiliaries such as surfactants, emulsifiers and stabilizers as well as a propellant gas. A preparation of this type usually contains the active substance in a concentration of about 0.1 to 10, in particular of about 0.3 to 3% by weight.

The dosage of the active substance of the formula I which is to be administered, and the frequency of administration depend on the strength of action and duration of action of the compounds used; and, in addition, on the nature and severity of the disease which is to be treated, as well as on the sex, age, weight and individual response of the mammal which is to be treated. On average, the recommended daily dose of a compound of the formula I for a patient weighing about 75 kg is at least 0.1 mg, at least 1 mg, up to a maximum of 100 mg, preferably up to a maximum of 10 mg. In this connection, several, for example up to 4, single doses a day may be necessary for acute episodes of the disease, for example for attacks of asthma or for renal colic, whereas just one dose may suffice for prophylaxis.

It is possible according to the invention to obtain, for example, the compounds of the formula I listed in the following table.

7-Nitro-trans-5-(2-oxo-pyrrolidin-1-yl)-2,3,4,5-tetrahydro-1-benzoxepin-4-ol
Trans-5-(2-oxo-pyrrolidin-1-yl)-7-phenylsulfinyl-2,3,4,5-tetrahydro-1-benzoxepin-4-ol
Trans-5-(2-oxo-pyrrolidin-1-yl)-7-phenylsulfonyl-2,3,4,5-tetrahydro-1-benzoxepin-4-ol
Trans-5-(2-oxo-pyrrolidin-1-yl)-7-phenylcarbonyl-2,3,4,5-tetrahydro-1-benzoxepin-4-ol
7-(2-Fluoro-phenylcarbonyl)-trans-5-(2-oxo-pyrrolidin-1-yl)-2,3,4,5-tetrahydro-1-benzoxepin-4-ol
7-Cyano-trans-5-(2-oxo-pyrrolidin-1-yl)-2,3,4,5-tetrahydro-1-benzoxepin-4-ol
7-Cyano-trans-5-(1,2-dihydro-2-oxo-pyrid-1-yl)-2,3,4,5-tetrahydro-1-benzoxepin-4-ol
Trans-5-(5-chloro-1,2-dihydro-2-oxo-pyrid-1-yl)-7-cyano-2,3,4,5-tetrahydro-1-benzoxepin-4-ol
7-Cyano-trans-5-(5-nitro-1,2-dihydro-2-oxo-pyrid-1-yl)-2,3,4,5-tetrahydro-1-benzoxepin-4-ol
Trans-5-(5-nitro-1,2-dihydro-2-oxo-pyrid-1-yl)-7-phenylsulfinyl-2,3,4,5-tetrahydro-1-benzoxepin-4-ol
Trans-5-(5-chloro-1,2-dihydro-2-oxo-pyrid-1-yl)-7-phenylsulfinyl-2,3,4,5-tetrahydro-1-benzoxepin-4-ol
Trans-5-(5-nitro-1,2-dihydro-2-oxo-pyrid-1-yl)-7-phenylsulfonyl-2,3,4,5-tetrahydro-1-benzoxepin-4-ol
Trans-5-(5-chloro-1,2-dihydro-2-oxo-pyrid-1-yl)-7-phenylsulfonyl-2,3,4,5-tetrahydro-1-benzoxepin-4-ol
Trans-5-(1,2-dihydro-2-oxo-pyrid-1-yl)-7-(4-chloro-phenylcarbonyl)-2,3,4,5-tetrahydro-1-benzoxepin-4-ol Where centers of asymmetry are present in the Examples detailed hereinafter, the relevant formulae depicted are intended to express only relative configurations.

The chemical shift is reported in ppm from TMS as internal standard.

EXAMPLE 1

Trans-5-(2-oxo-pyrrolidin-1-yl)-2,3,4,5-tetrahydro-1-benzoxepin-4-ol

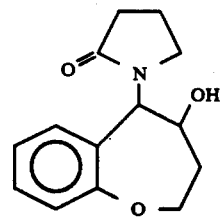

3.24 g (20 mmol) of 4,5-epoxy-2,3,4,5-tetrahydro-1-benzoxepin and 9.60 g (61 mmol) of N-trimethylsilyl-2-oxo-pyrrolidine are dissolved in 8 ml of dry THF and, while cooling, 6.31 g (20 mmol) of tetrabutylammonium fluoride trihydrate are added in one portion, and the mixture is heated at 100° C. for several hours (TLC check). The mixture is hydrolyzed with ice-water and extracted several times with diethyl ether. The combined diethyl ether extracts are washed with saturated sodium chloride solution and dried over sodium sulfate. After filtration and evaporation of the solvent in vacuo, the residue is crystallized in diisopropyl ether/ethyl acetate. Crystals of melting point 151°–153° C. are obtained.

$C_{14}H_{17}NO_3$ (247.298): Calc. C 68.00 H 6.93 N 5.66
Found C 67.9 H 7.0 N 5.6

EXAMPLE 2

7-Chloro-trans-5-(2-oxo-pyrrolidin-1-yl)-2,3,4,5-tetrahydro-1-benzoxepin-4-ol

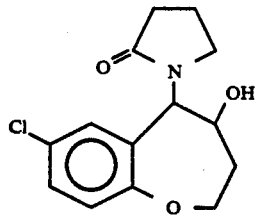

5 ml (5 mmol) of lithium bis-(trimethylsilyl)-amide (1M solution in THF) are added dropwise with stirring to 1.40 g (5 mmol) of trans-5-bromo-7-chloro-4-hydroxy-2,3,4,5-tetrahydro-1-benzoxepin at 0° C. under argon. After stirring for 2 hours, 0.43 g (5 mmol) of 2-pyrrolidinone and subsequently a further 5 ml of lithium bis-(trimethylsilyl)-amide are added, and the mixture is heated at 110° C. for several hours (TLC check). The mixture is poured onto ice-water and extracted several times with ethyl acetate. The combined ethyl acetate extracts are washed with water and saturated sodium chloride solution, dried over sodium sulfate, filtered and evaporated in vacuo. The residue is triturated with hot methanol/ethyl acetate and filtered off with suction. Crystals of melting point 186°–188° C. are obtained.

$C_{14}H_{16}ClNO_3$ (281.747): Calc. C 59.68 H 5.72 N 4.97 Found C 59.4 H 5.7 N 4.9

EXAMPLE 3

Trans-5-(1,2-dihydro-2-oxo-pyrid-1-yl)-2,3,4,5-tetrahydro-1-benzoxepin-4-ol

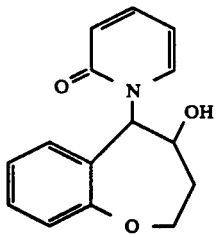

6.40 g (20 mmol) of tetrabutylammonium fluoride trihydrate are added to a mixture of 3.24 g (20 mmol) of 4,5-epoxy-2,3,4,5-tetrahydro-1-benzoxepin and 10 g (60 mmol) of 2-trimethylsilyoxy-pyridine, and the mixture is heated at 80°–90° C. with stirring. After a reaction time of 5 hours, the mixture is slowly stirred into ice-water, and the precipitated solid is filtered off with suction and recrystallized from methanol with the addition of small amounts of dioxane. Crystals of melting point 232°–234° C. are obtained.

$C_{15}H_{15}NO_3$ (257.29): Calc. C 70.02 H 5.88 N 5.44 Found C 70.1 H 5.9 N 5.4

$^1$H NMR (60 MHz/d$^6$-DMSO): δ=7.67–6.63 (m, 6H); δ=6.53–5.93 (m, 3H); δ=5.23 (d,J=5 Hz, 1H); δ=4.50–3.63 (m,3H); δ=2.27–1.77 (m,2H).

EXAMPLE 4

Trans-5-(5-chloro-1,2-dihydro-2-oxo-pyrid-1-yl)-2,3,4,5-tetrahydro-1-benzoxepin-4-ol

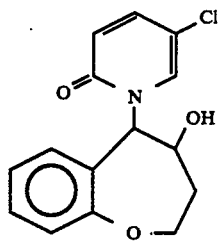

22.7 g (72 mmol) of tetrabutylammonium fluoride trihydrate are added to a mixture of 10.54 g (65 mmol) of 4,5-epoxy-2,3,4,5-tetrahydro-1-benzoxepin and 19.4 g (96 mmol) of 5-chloro-2-trimethylsilyloxy-pyridine, and the mixture is heated at 90° C. for 3 hours. The mixture is stirred into water and extracted several times with ethyl acetate. The combined organic phases are washed with water and saturated sodium chloride solution, and the solvent is evaporated off in vacuo. The residue is crystallized in n-butyl acetate. Crystals of melting point 175.5°–177.5° C. are obtained.

$C_{15}H_{14}ClNO_3$ (291.74); Calc. C 61.75 H 4.84 N 4.80 Found C 61.7 H 4.9 N 4.8

$^1$H NMR (270 MHz/d$^6$-DMSO): δ=7.83 (d, J=3 Hz, 1H), δ=7.53 (d,d, J$_1$=10 Hz, J$_2$=3 Hz, 1H); δ=7.28 (t,d, J$_1$=8 Hz, J$_2$=1 Hz, 1H); δ=7.07 (t, J=8 Hz, 1H); δ=7.06 (t,d, J$_1$=8 Hz, J$_2$=1 Hz, 1H); δ=6.75 (d, J=8 Hz, 1H); δ=6.52 (d, J=10 Hz, 1H); δ=5.98 (d, J=5 Hz, 1H); δ=5.35 (d, J=5 Hz, 1H); δ=4.25 (m, 2H); δ=3.88 (d,d,d, J$_1$=10, J$_2$=J$_3$=3 Hz, 1H); δ=2.18–1.92 (m, 2H).

EXAMPLE 5

Trans-5-(1,2-dihydro-5-nitro-2-oxo-pyrid-1-yl)-2,3,4,5-tetrahydro-1-benzoxepin-4-ol

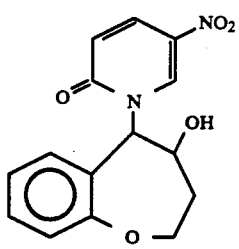

7.85 g (56 mmol) of 2-hydroxy-5-nitro-pyridine are added in portions to 1.61 g (56 mmol) of sodium hydride (80% dispersion in mineral oil) in 30 ml of DMPU (1,3-dimethyl-tetrahydro-2(1H)-pyrimidinone) under argon. After evolution of gas has ceased the mixture is stirred for 20 minutes. Then, at room temperature, a solution of 4,5-epoxy-2,3,4,5-tetrahydro-1-benzoxepin in 10 ml of DMPU is added dropwise. The mixture is subsequently heated at 95° C. for 6 hours. The mixture is poured into ice/water, stirring vigorously, and precipitated solid is filtered off with suction. The solid is chromatographed on silica gel (ethyl acetate/cyclohexane 2:1), and the pale yellow oil obtained in this way is crystallized in methyl tert.-butyl ether. Melting point 152°–155° C.

$C_{15}H_{14}N_2O_5$ (302.29): Calc.: C 59.60 H 4.67 N 9.27 Found: C 59.5 H 4.6 N 9.0

$^1$H NMR (270 MHz/d$^6$-DMSO): δ=8.93 (d, J=3 Hz, 1H); δ=8.19 (d,d, J=10 Hz, J$_2$=3 Hz, 1H); δ=7.32 (t,d, J$_1$=8 Hz, J$_2$=1 Hz, 1H); δ=7.11 (d, J=8 Hz, 1H); δ=7.07 (t,d, J$_1$=8 Hz, J$_2$=1 Hz, 1H); δ=6.89 (d, J=8 Hz, 1H); δ=6.61 (d, J=10 Hz, 1H); δ=6.09 (d, J=8 Hz, 1H); δ=5.51 (d, J=6 Hz, 1H); δ=4.31 (m, 2H); δ=3.95 (d,d,d, J$_1$=8 Hz, J$_2$=J$_3$=3 Hz, 1H); δ2.16 (m, 1H), δ=1.99 (m, 1H).

EXAMPLE 6

7-nitro-trans-5-(5-chloro-1,2-dihydro-2-oxo-pyrid-1-yl)-2,3,4,5-tetrahydro-1-benzoxepin-4-ol

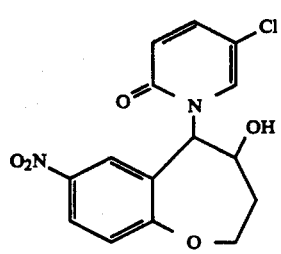

6.63 g (21 mmol) of tetrabutylammonium fluoride trihydrate are added to a stirred mixture of 3.93 g (19 mmol) of 4,5-epoxy-7-nitro-2,3,4,5-tetrahydro-1-benzoxepin and 8.06 g (40 mmol) of 5-chloro-2-trimethylsilyl-pyridine, and the mixture is heated at 60° C. for 5 hours. The mixture is then stirred into ice-water and extracted several times with ethyl acetate. The combined ethyl acetate extracts are washed with water and saturated sodium chloride solution dried over sodium sulfate, filtered and evaporated in vacuo. The remaining viscous oil crystallizes after standing for some time. It is triturated with ethyl acetate and filtered off with suction. Crystals of melting point 219°–222° C. are obtained.

$C_{15}H_{13}ClN_2O_5$ (336.74) Calc.: C 53.50 H 3.89 N 8.32 Found: C 53.3 H 3.9 N 8.2

$^1$H NMR (270 MHz/d$^6$-DMSO): δ=8.16 (d,d, J$_1$=8 Hz, J$_2$=3 Hz, 1H); δ=7.99 (d, J=3 Hz, 1H); δ=7.60 (d,d, J$_1$=10 Hz, J$_2$=3 Hz, 1H); δ=7.51 (d, J=3 Hz, 1H); δ=7.27 (d, J=8 Hz, 1H); δ=6.57 (d, J=10 Hz, 1H); δ=6.00 (d, J=9 Hz, 1H); δ=5.49 (d, J=6 Hz, 1H); δ=4.51 (m, 1H); δ=4.40 (m, 1H); δ=4.04 (m, 1H); δ=2.21 (m, 1H); δ=2.04 (m, 1H).

EXAMPLE 7

7-Nitro-trans-5-(1,2-dihydro-2-oxo-pyrid-1-yl)-2,3,4,5-tetrahydro-1-benzoxepin

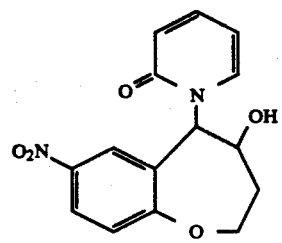

The compound is obtained in analogy to Example 6. Melting point 200°–203° C.

$C_{15}H_{14}N_2O_5$ (302.29) Calc.: C 59.60 H 4.67 N 9.27 Found: C 59.5 H 4.9 N 9.0

$^1$H NMR (270 MHz/d$^6$-DMSO): δ=8.14 (d,d, J$_1$=8 Hz, J$_2$=3 Hz, 1H); =7.74 (d,d, J$_1$=7 Hz J$_2$=1 Hz, 1H); δ=7.56–7.49 (m, 2H); δ=7.25 (d, J=8 Hz, 1H); δ=6.5 (d, J=10 Hz, 1H); δ=6.37 (t,d, J$_1$=7 Hz, J$_2$=1 Hz, 1H); δ=6.10 (d, J=8 Hz, 1H); δ=5.54 (brS, 1H); δ=4.53 (m, 1H); δ=4.41 (m, 1H); δ=4.07 (m, 1H); δ=2,21 (m, 1H); δ=2.05 (m, 1H).

EXAMPLE 8

Trans-5-(1,2-dihydro-2-oxo-pyrid-1-yl)-7-phenylsulfinyl-2,3,4,5-tetrahydro-1-benzoxepin-4-ol

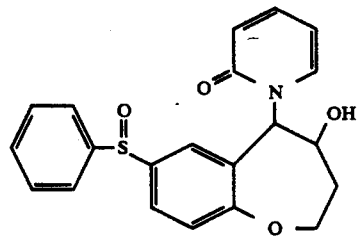

8.60 g (27.3 mmol) of tetrabutylammonium fluoride trihydrate are added to a mixture of 4.00 g (10.9 mmol) of trans-4-bromo-5-hydroxy-7-phenylsulfinyl-2,3,4,5-tetrahydro-1-benzoxepin and 6.40 g (38.3 mmol) of 2-trimethylsilyloxypyridine, and a mixture is subsequently stirred at 60° C. for 5 hours. The cooled syrupy liquid is poured onto ice-water and extracted several times with ethyl acetate. The combined ethyl acetate extracts are washed with water and saturated sodium chloride solution, dried over sodium sulfate, filtered and evaporated. The foamy residue is crystallized in butyl acetate. White crystals of melting point 181°–184° C. are obtained.

$C_{21}H_{19}NO_4S$ (381.45) Calc.: C 66.1 H 5.0 N 3.6 Found: C 65.5 H 5.1 N 3.5

$^1$H NMR (270 MHz/d$^6$-DMSO): δ=7.62–7.43 (m, 8H); δ=7.18 (d,d, J$_1$=8 Hz, J$_2$=3 Hz, 1H); δ=7.01 (d, J=2 Hz, 1H); δ=6.45 (m, 1H); 6.28 (m, 1H); 6.05 (d, J=8 Hz, 1H); δ=5.33 (d,d, J$_1$=6 Hz, J$_2$=2 Hz, 1H); δ=4.34 (m, 1H); δ=4.21 (m, 1H); δ=3.94 (m, 1H); δ=2.18–2.06 (m, 1H); δ=2.04–1.90 (m, 1H).

EXAMPLE 9

Trans-5-(1,2-dihydro-2-oxo-pyrid-1-yl)-7-phenylsulfonyl-2,3,4,5-tetrahydro-1-benzoxepin-4-ol

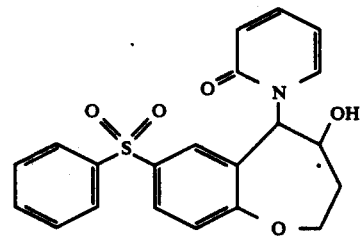

is obtained in analogy to Example 8 from trans-4-bromo-5-hydroxy-7-phenylsulfonyl-2,3,4,5-tetrahydro-1-benzoxepin. Melting point 190°–193° C. (after extraction by stirring in ethyl acetate).

$C_{21}H_{19}NO_5S$ (397.46) Calc.: C 63.4 H 4.81 N 3.52 Found: C 63.1 H 4.9 N 3.6

¹H NMR (270 MHz/d⁶-DMSO): δ=7.86–7.77 (m, 3H); δ=7.72–7.46 (m, 5H); δ=7.22 (d, J=8 Hz, 1H); δ=7.19 (d, J=2 Hz, 1H); δ=6.48 (d, J=10 Hz, 1H); δ=6.34 (t, d, J₁=6 Hz, J2=1 Hz, 1H); δ=6.04 (d, J=8 Hz, 1H); δ=5.36 (d, J=6 Hz, 1H); δ=4.41 (m, 1H); δ=4.27 (m, 1H); δ=3.99 (m, 1H); δ=2.27–2.10 (m, 1H); δ=2.07–1.92 (m, 1H).

EXAMPLE 10

Trans-5-(1,2-dihydro-2-oxo-pyrid-1-yl)-7-(2-fluorobenzoyl)-2,3,4,5-tetrahydro-1-benzoxepin-4-ol

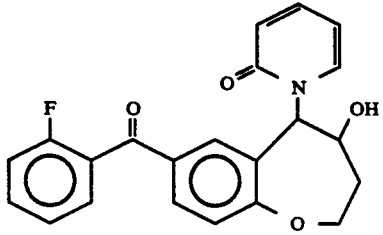

is obtained in analogy to Example 8 from trans-4-bromo-5-hydroxy-7-(2-fluorobenzoyl)-2,3,4,5-tetrahydro-1-benzoxepin. Melting point 219°–221° C. (methanol).

C22H18F1O4 (379.39) Calc.: C 69.6 H 4.78 N 3.69
Found: C 69.3 H 4.9 N 3.7

¹H NMR (270 MHz/d⁶-DMSO): δ=7.69–7.56 (m, 3H); δ=7.47–7.27 (m, 4H); δ=7.18 (d, J=8 Hz, 1H); δ=7.12 (sbr, 1H); δ=6.42 (d, J=10 Hz, 1H); δ=6.24 (t, d, J₁=7 Hz, J2=2 Hz, 1H); δ=6.10 (d, J=8 Hz, 1H); δ=5.35 (d, J=6 Hz, 1H); δ=4.47 (m, 1H); δ=4.27 (m, 1H); δ=4.01 (m, 1H); δ=2.21 (m, 1H); δ=2.06 (m, 1H).

EXAMPLE 11

Trans-5-(1,2-dihydro-2-oxo-pyrid-1-yl)-7-(2-trifluoromethyl-benzoyl)-2,3,4,5-tetrahydro-1-benzoxepin-4-ol

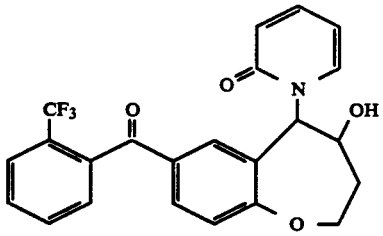

is obtained in analogy to Example 8 from trans-4-bromo-5-hydroxy-7-(2-trifluoromethyl-benzoyl)-2,3,4,5-tetrahydro-1-benzoxepin. Melting point 176°–179° C. (methyl tert.butyl ether).

C23H18F3N1O4 (429.41) Calc.: C 64.33 H 4.2 N 3.2
Found: C 64.6 H 4.1 N 3.1

¹H NMR (270 MHz/CDCl3): δ=7.74 (m, 2H); δ=7.63–7.49 (m, 3H); δ=7.37–7.24 (m, 3H); δ=7.16 (d, J=8 Hz, 1H); δ=6.55 (d, J=10 Hz, 1H); δ=6.15 (m, 2H); δ=4.45 (m, 1H); δ=4.38–4.15 (m, 3H); δ=2.27–2.01 (m, 2H).

EXAMPLE 12

Trans-7-nitro-5-(2-oxo-pyrrolidin-1-yl)-2,3,4,5-tetrahydro-1-benzoxepin-4-ol

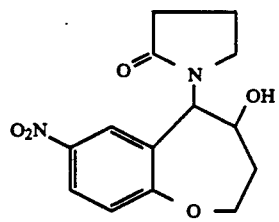

6.22 g (30 mmol) of 4,5-epoxy-7-nitro-2,3,4,5-tetrahydro-1-benzoxepin are suspended in 28.3 g (180 mmol) of N-trimethylsilyl-2-oxo-pyrrolidine, and 0.95 g (3 mmol) of tetrabutylammonium fluoride trihydrate is added. The mixture becomes dark brown and homogeneous after a short time. The mixture is stirred at room temperature until reaction is complete (TLC check). The mixture is hydrolyzed and extracted several times with ethyl acetate, and the combined ethyl acetate extracts are washed with water and saturated sodium chloride solution. The residue after drying over sodium sulfate and evaporation of the solvent in vacuo is stirred with diethyl ether. The crystals which have separated out are filtered off with suction and washed with a little cold diethyl ether.

Yield: 7.30 g of trans-7-nitro-5-(2-oxo-pyrrolidin-1-yl)-4-trimethylsilyloxy-2,3,4,5-tetrahydro-1-benzoxepin of melting point 159°–161° C.

C17H24N2O5Si (364.48) Calc.: C 56.02 H 6.63 N 7.68
Found: C 56.1 H 6.6 N 7.8

¹H NMR (270 MHz/d⁶-DMSO): δ [ppm] from trimethylsilyl group δ=8.04 (d,d, J₁=8 Hz, J2=3 Hz, 1H); δ=7.58 (d, J=3 Hz, 1H); δ=7.18 (d, J=8 Hz, 1H); δ=5.29 (s, 1H); δ=4.35 (d, br, J=4 Hz, 1H); δ=4.30 (d, t, J₁=12 Hz, J2=4 Hz, 1H); δ=3.81 (t, d, J₁=12 Hz, J2=2 Hz, 1H); δ=3.55 (m, 2H); δ=2.41–1.90 (m, 6H); δ=0 (s, 9H).

For elimination of the silyl group, 5.09 g (14 mmol) of the above silyl compound are dissolved in 15 ml of absolute THF, and 4.42 g (14 mmol) of tetrabutylammonium fluoride trihydrate are added. The mixture is stirred for 1 hour, hydrolyzed with dilute ammonium chloride solution and extracted several times with ethyl acetate. The combined ethyl acetate extracts are washed with water and saturated sodium chloride solution and dried over sodium sulfate, and the solvent is evaporated off in vacuo. The residue is triturated with diisopropyl ether, and the crystals are filtered off with suction.

Yield: 3.65 g.

Melting point 179°–181° C.

C14H16N2O5 (292.29) Calc.: C 57.53 H 5.5 N 9.58
Found: C 57.2 H 5.5 N 9.6

¹H NMR (270 MHz/d⁶-DMSO): δ=8.08 (d,d, J₁=8 Hz, J2=3 Hz, 1H); δ=7.63 (d, J=3 Hz, 1H); δ=7.21 (d, J=8 Hz, 1H); δ=5.25 (s, 1H); δ=5.20 (d, J=4 Hz, 1H); δ=4.33 (d, t, J₁=12 Hz, J2=4 Hz, 1H); δ=4.23 (sbr, 1H); δ=3.93 (t, d, J₁=12 Hz, J2=2 Hz, 1H); δ=3.69 (t, J=7 Hz, 2H); δ=2.38 (m, 2H); δ=2.31–2.03 (m, 3H); δ=1.91 (m, 1H).

EXAMPLE 13

Trans-7-cyano-5-(2-oxo-pyrrolidin-1-yl)-2,3,4,5-tetrahydro-1-benzoxepin-4-ol

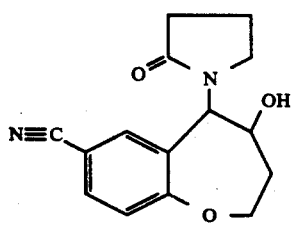

is prepared from 7-cyano-4,5-epoxy-2,3,4,5-tetrahydro-1-benzoxepin in a manner analogous to that described in Example 12.

Melting point 168°-170° C. (isopropanol).

$C_{15}H_{16}N_2O_3$ (272.31) Calc.: 66.16 H 5.92 N 10.29 Found: C 65.8 H 5.9 N 10.0

$^1$H NMR (270 MHz/d$^6$-DMSO): δ=7.70 (d,d, J$_1$=8 Hz, J$_2$=3 Hz, 1H); δ=7.45 (d, J=3 Hz, 1H); δ=7.12 (d, J=8 Hz, 1H); δ=5.24 (d, J=5 Hz, 1H); δ=5.11 (d, J=8 Hz, 1H); δ=4.33 (t, d, J$_1$=12 Hz, J$_2$=2 Hz, 1H); δ=4.03 (m, 2H); δ=3.59 (m, 1H); δ=3.23 (m, 1H); δ=2.31 (t, J=8 Hz, 2H); δ=2.14 (m, 1H); δ=2.06–1.81 (m, 3H).

EXAMPLE 14

Trans-7-nitro-5-(5-(R,S)-methyl-2-oxo-pyrrolidin-1-yl)-2,3,4,5-tetrahydro-1-benzoxepin-4-ol

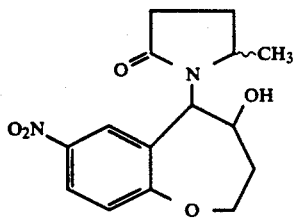

is prepared in analogy to Example 12 from 4,5-epoxy-7-nitro-2,3,4,5-tetrahydro-1-benzoxepin.

Starting from 10.4 g (50 mmol) of 4,5-epoxy-7-nitro-2,3,4,5-tetrahydro-1-benzoxepin, 6.7 g of trans-7-nitro-5-(5-(R,S)-methyl-2-oxo-pyrrolidin-1-yl)-4-trimethylsilyloxy-2,3,4,5-tetrahydro-1-benzoxepin melting in the range 179°-185° C. are isolated. After elimination of the silyl group and after crystallization and chromatography on silica gel (ethyl acetate/cyclohexane 7:3) the diastereomers A and B are obtained.

Diastereomer B: melting point 198°-200° C.

$^1$H NMR (270 MHz/d$^6$-DMSO): δ=8.11 (d,d, J$_1$=8 Hz, J$_2$=3 Hz, 1H); δ=7.76 (d, J=3 Hz, 1H); δ=7.24 (d, J=8 Hz, 1H); δ=5.65 (sbr, 1H); δ=4.98 (sbr, 1H); δ=4.38–4.29 (m, 2H); δ=4.02 (m, 1H); δ=3.87 (t, d, J$_1$=12 Hz, J$_2$=2 Hz, 1H); δ=2.72-2.59 (m, 1H); δ=2.52-2.25 (m, 3H); δ=1.89 (m, 1H); δ=1.75 (m, 1H); δ=1.02 (d, J=7 Hz, 3H).

Diastereomer A: melting point 145°-147° C.

$^1$H NMR (270 MHz/d$^6$-DMSO): δ=8.11 (d,d, J$_1$=8 Hz, J$_2$=3 Hz, 1H); δ=7.73 (d, J=3 Hz, 1H); δ=7.24 (d, J=8 Hz, 1H); δ=5.76 (sbr, 1H); δ=4.91 (sbr, 1H); δ=4.34 (d, t, J$_1$=12 Hz, J$_2$=3.5 Hz, 1H); δ=4.27 (m, 1H); δ=3.92 (t, d, J$_1$=12 Hz, J$_2$=2 Hz, 1H); δ=3.78 (m, 1H); δ=2.59 (m, 1H); δ=2.52-2.24 (m, 3H); δ=1.92 (dbr, J=14 Hz, 1H); δ=1.75 (m, 1H); δ=1.28 (d, J=7 Hz, 3H).

Preparation of Precursors

4-Phenoxybutyryl chloride

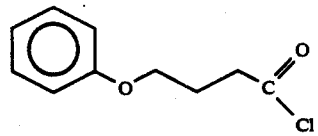

252.3 g (1.40 mole) of 4-phenoxybutyric acid, 154 ml (2.1 mole) of thionyl chloride and a few drops of dimethylformamide are heated under reflux with exclusion of moisture. After evolution of gas has ceased (about 2 hours), the mixture is fractionated under water pump vacuum. The acid chloride distils at 149°-151° C.

Yield: 238 g=1.2 mole (86% of theory).

2,3-Dihydro-1-benzoxepin-5(4H)-one

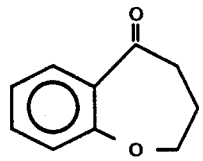

A solution of 238 g (1.2 mole) of 4-phenoxybutyryl chloride, dissolved in 350 ml of 1,2-dichloroethane, is added dropwise to a suspension, cooled to 0° C., of 192 g of aluminum trichloride in 1,200 ml of 1,2-dichloroethane within 4.5 hours while passing through nitrogen and stirring vigorously. The mixture is then stirred at 0° C. for 1.5 hours and allowed to warm to room temperature overnight. The mixture is added to a stirred mixture of 2,000 ml of concentrated hydrochloric acid and 2.5 kg of ice and then stirred for 1.5 hours. The aqueous phase is decanted off, and insoluble residue is removed from the organic phase by filtration, washing thoroughly with 1,2-dichloroethane. The aqueous phase is extracted 3–4 times more with methylene chloride, and the combined organic phases are washed with saturated sodium bicarbonate solution, water and saturated sodium chloride solution and dried over sodium sulfate. A yellowish oil is obtained after the solvent has been evaporated off in vacuo and is dissolved in diethyl ether, and the last residues of dyestuff are removed by filtration. Evaporation in vacuo results in a clear oil which distils at 74°-75° C./0.02 torr.

Yield: 121.9 g=753 mmol (63% of theory).

$^1$H NMR (60 MHz/CDCl$_3$): δ=7.83–6.88 (m, 4H); δ=4.23 (t, 2H); δ=2.90 (t, 2H); 2.23 (q, 2H).

5-Hydroxy-2,3,4,5,-tetrahydro-1-benzoxepin

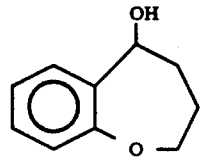

121.9 g (0.752 mole) of 2,3-dihydro-1-benzoxepin-5(4H)-one are dissolved in 1,400 ml of methanol and, while stirring vigorously, 18.5 g (0.489 mole) of sodium borohydride are introduced in portions so that the temperature remains below 20° C. The mixture is subsequently stirred for 2 hours, most of the solvent is distilled off in vacuo, and the residue is taken up in ethyl acetate. The organic phase is washed with water, 1N potassium bisulfate solution, water and saturated sodium chloride solution and dried over sodium sulfate. The mixture is filtered, and the solvent is evaporated off in vacuo. The oil crystallizes after some time.

Melting point: 60°-68.5° C.

Yield: 120 g=732 mmol (97% of theory).

$^1$H NMR (60 MHz/CDCl$_3$): δ=7.47–6.78 (m, 4H); δ=4.93–4.73 (m, 1H); δ=4.13–4.87 (m, 2H); δ=2.35 (brs, 1H); δ=2.27–1.70 (m, 4H).

2,3-Dihydro-1-benzoxepin

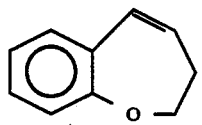

800 ml of toluene are poured over 53 g (0.323 mole) of 5-hydroxy-2,3,4,5-tetrahydro-1-benzoxepin and, with addition of 3.7 g of p-toluenesulfonic acid monohydrate, the mixture is refluxed with a water trap for 1.5 hours. The cold organic phase is washed with saturated sodium bicarbonate solution, water and sodium chloride solution, and the solvent is evaporated off in vacuo. Kugelrohr distillation at 30°-35° C./0.008 torr results in 44 g of oil. p $^1$H NMR (60 MHz/CDCl$_3$): δ=7.23–6.70 (m, 4H); δ=6.30 (m, 1H); δ=6.07–5.70 (m, 1H); δ=4.20 (t, J=5 Hz, 2H); δ=2.63 (m, 2H).

Trans-4-bromo-5-hydroxy-2,3,4,5-tetrahydro-1-benzoxepin

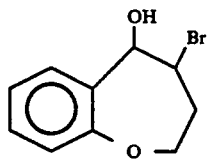

64.2 g (0.44 mole) of 2,3-dihydro-1-benzoxepin are dissolved in a mixture of 1,800 ml of dimethyl sulfoxide and 180 ml of water and cooled to 10°-12° C. Then, while stirring vigorously, 156.6 g (0.88 mole) of N-bromosuccinimide are added in one portion, and the temperature is controlled so that 25° C. is not exceeded. After 1 hour, the mixture is poured onto ice/water and extracted 3 times with diethyl ether. The combined organic phases are washed with water and saturated sodium chloride solution and dried over sodium sulfate. After filtration, the solvent is evaporated off in vacuo, and the remaining yellowish oil is crystallized in cyclohexane.

Yield: 63.0 g=0.259 mmol=59% of theory.

$^1$H NMR (60 MHz/CDCl$_3$): δ=7.50–6.85 (m, 4H); δ=4.88 (d, J=7 Hz, 1H); δ=4.58–4.30 (m, 1H); δ=4.23–4.00 (m, 2H); δ=3.13–1.93 (m, 3H).

4,5-Epoxy-2,3,4,5-tetrahydro-1-benzoxepin

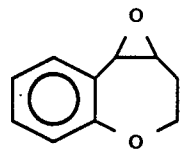

8.60 g (0.298 mole) of sodium hydride (80% dispersion in mineral oil) are introduced under argon into 320 ml of DMSO, and a solution of 243 g (0.259 mole) of trans-4-bromo-5-hydroxy-2,3,4,5-tetrahydro-1-benzoxepin in 180 ml of DMSO is added dropwise at room temperature within 2.5 hours. After 3 hours, the mixture is poured onto ice/water with stirring, and is extracted 3 times with diethyl ether. The combined organic phases are washed with water and saturated sodium chloride solution, dried over sodium sulfate and filtered, and the solvent is evaporated off in vacuo. The remaining 44 g of oil is distilled at 67°-69° C./0.01 torr.

Yield: 37.1 g=0.229 mole (88% of theory).

$^1$H NMR (60 MHz/CDCl$_3$): δ=7.50–6.73 (m, 4H); δ=4.17–3.80 (m, 3H); δ=3.73–3.53 (m, 1H); δ=2.66–2.37 (m, 2H).

2,3-Dihydro-7-nitro-1-benzoxepin-5(4H)-one

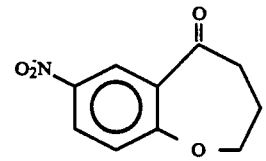

40.5 g (0.25 mole) of 2,3-dihydro-1-benzoxepin-5(4H)-one are introduced at −10° C. into 400 ml of concentrated sulfuric acid while stirring. Coarsely crystalline sodium nitrate is slowly introduced at −5° C. to 0° C. whilst stirring vigorously. The mixture is then stirred at 0° C. for about 1 hour, during which the sodium nitrate slowly dissolves. The mixture is stirred into ice/water and, after about 30 minutes, filtered with suction and washed thoroughly with water. The residue on the filter is taken up in ethyl acetate, and the solution is separated from the water, dried over sodium sulfate, filtered and evaporated in vacuo. The residue is crystallized in ethyl acetate/cyclohexane.

Melting point: 112°-120° C.

Yield: 32.1 g=0.156 mole (62% of theory).

$^1$H NMR (60 MHz/CDCl$_3$): δ=8.67 (d, J=3 Hz, 1H); δ=8.27 (d,d, J$_1$=9 Hz, J$_2$=3 Hz, 1H); J=9 Hz, 1H); δ=4.38 (t, J=7 Hz, 2H); δ=2.95 (t, d, J$_1$=7 Hz, J$_2$=1 Hz, 2H); δ=2.32 (m, 2H).

5-Hydroxy-7-nitro-2,3,4,5-tetrahydro-1-benzoxepin

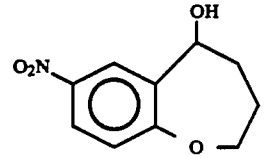

32.1 g (0.155 mole) of 2,3-dihydro-7-nitro-1-benzoxepin-5(4H)-one are suspended in 220 ml of methanol and, while stirring at 0° C. under argon, 6.5 g (0.17 mole) of sodium borohydride are added in portions. The mixture is then stirred for about 30 minutes and stirred into ice/water, and the precipitated solid is filtered off with suction and thoroughly washed with water. The solid is taken up in the ethyl acetate, and the solution is separated from the water, dried over sodium sulfate, filtered and evaporated in vacuo. The residue is crystallized in diisopropyl ether/cyclohexane with the addition of active charcoal.

Melting point: 83°-85° C.

Yield: 23 g=0.11 mole (71% of theory).

$^1$H NMR (60 MHz/CDCl$_3$): δ=8.43 (d, J=3 Hz, 1H); δ=8.10 (d,d, J$_1$=9 Hz, J$_2$=3 Hz, 1H); δ=7.10 (d, J=9 Hz, 1H); δ=5.23-4.83 (m, 1H); δ=4.53-3.60 (m, 2H); δ=2.40-1.73 (m, 5H).

2,3-Dihydro-7-nitro-1-benzoxepin

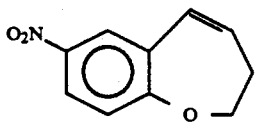

300 ml of toluene are poured over 25.1 g (0.12 mole) of 5-hydroxy-7-nitro-2,3,4,5-tetrahydro-1-benzoxepin and, with the addition of 1.5 g of p-toluenesulfonic acid, the mixture is refluxed with a water trap for 2 hours. The cold reaction solution is washed with saturated sodium bicarbonate solution, water and saturated sodium chloride solution, dried over sodium sulfate and filtered, and the solvent is evaporated off in vacuo. The residue is a solid of melting point 94°-95.5° C.

Yield: 22 g=0.115 mole (96% of theory).

Trans-4-bromo-5-hydroxy-7-nitro-2,3,4,5-tetrahydro-1-benzoxepin

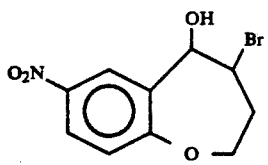

22.9 g (0.12 mole) of 2,3-dihydro-7-nitro-1-benzoxepin in a mixture of 460 ml of dimethyl sulfoxide and 46 ml of water are cooled to about 12° C. and, while stirring vigorously, 42.7 g (0.24 mole) of N-bromo-succinimide are added, during which the temperature is kept below 25° C. The mixture is then stirred at room temperature for about 30 minutes and stirred into ice/water and extracted with diethyl ether. The combined organic phases are washed with water and saturated sodium chloride solution, dried over sodium sulfate and filtered, and the solvent is evaporated off in vacuo. The solid residue is triturated with cyclohexane and filtered off with suction.

Yield: 32.2 g (0.112 mole=93% of theory).

Melting point: 105°-106.5° C.

4,5-Epoxy-7-nitro-2,3,4,5-tetrahydro-benzoxepin

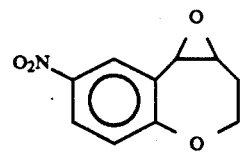

2.65 g (0.115 mole) of metallic sodium are dissolved in 220 ml of methanol and, while stirring, a solution of 31.7 g (0.11 mole) of trans-4-bromo-5-hydroxy-7-nitro-2,3,4,5-tetrahydro-1-benzoxepin in 230 ml of methanol is added dropwise at room temperature. After 2.5 hours the precipitated solid is filtered off with suction and washed with methanol, and the filtrate is evaporated in vacuo. The residue is a solid of melting point 121°-123° C.

Yield: 17.9 g=86.5 mmol (79% of theory).

$^1$H NMR (60 MHz/CDCl$_3$): δ=8.48 (d, J=3 Hz, 1H); δ=8.07 (d,d, J=9 Hz, 1H); δ=7,02 (d, J=9 Hz, 1H); δ=4.33-3.93 (m, 3H); 3.83-3.62 (m, 1H); δ=2.67-2.37 (m, 2H).

7-Bromo-2,3-tetrahydro-1-benzoxepin

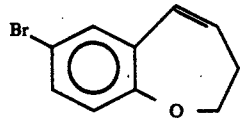

125 g (0.762 mole) of 5-hydroxy-2,3,4,5-tetrahydro-1-benzoxepin are dissolved in 938 ml of glacial acetic acid and cooled to 10° C. and, while stirring vigorously, 135.3 g (0.760 mole) of N-bromosuccinimide are introduced within 30 minutes, during which the temperature is kept below 20° C. The mixture is then stirred at 20° C. for 3 hours and poured into 3 l of ice/water while stirring vigorously, and the mixture is filtered with suction and washed thoroughly with water. The residue is again thoroughly triturated with water and filtered with suction. 1,700 ml of toluene is poured over the wet crude product and, with the addition of 2.00 g of p-toluenesulfonic acid monohydrate, the mixture is refluxed with a water trap for 3 hours. The solvent is evaporated off in vacuo, and the residue is filtered through silica gel. The mobile phase is initially cyclohexane and then cyclohexane/methyl tert.-butyl ether (200:1). The residue after evaporation of all the fractions in vacuo is a pale oil.

Yield: 126 g=0.56 mole (73% of theory).

$^1$H NMR (CDCl$_3$/60 MHz): δ=7.23 (sbr, 1H); δ=7.13 (d,d, J$_1$=9 Hz, J$_2$=3 Hz, 1H); δ=7.77 (dbr, J=9 Hz, 1H); δ=6.37-5.73 (m, 2H); δ=4.18 (t, J=5 Hz, 2H); δ=2.8-2.43 (m, 2H).

2,3-Dihydro-7-phenylthio-1-benzoxepin

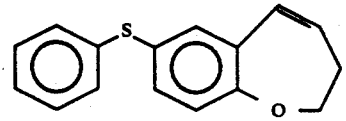

20 g (89.3 mmol) of 7-bromo-2,3-dihydro-1-benzoxepin are dissolved in 180 ml of dry tetrahydrofuran and, at −78° C. under argon, 105 ml (178.6 mmol) of tert.- butyllithium are added dropwise within 1 hour. The mixture is stirred at −78° C. for 4.5 hours and then, at this temperature, 19.6 g (89 mmol) of diphenyl disulfide dissolved in 90 ml of dry tetrahydrofuran are added dropwise. The temperature is allowed to rise to 0° C. over about 15 hours, and the mixture is hydrolyzed with cold water and extracted several times with diethyl ether. The combined organic extracts are washed with cold 5% strength potassium hydroxide solution, water and saturated sodium chloride solution. The solution is dried over sodium sulfate and filtered, and the solvent is evaporated off in vacuo. The remaining brown oil is filtered through a short silica gel column, (200 g) with cyclohexane. The residue after evaporation of all the fractions is 13.6 g = 53.3 mmol (60% of theory) of pale oil.

$^1$H NMR (CDCl$_3$/60 MHz): δ=7.80–6.77 (m, 8H); δ=6.53–5.77 (m, 2H); δ=4.25 (t, J=5 Hz, 2H); δ=2.83–2.47 (m, 2H).

2,3-Dihydro-7-phenylsulfinyl-1-benzoxepin

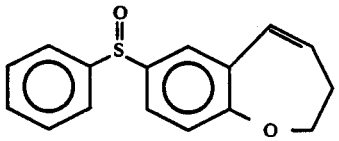

6.00 g (23.6 mmol) of 2,3-dihydro-7-phenylthio-1-benzoxepin are introduced at 15°-20° C. into 59 ml of glacial acetic acid and, at this temperature, 5 ml of aqueous hydrogen peroxide solution (30% strength) are added dropwise. The mixture is stirred at this temperature for about 2 hours until all the precursor has reacted (TLC check). The mixture is then stirred into sodium bicarbonate/ice-water and extracted several times with diethyl ether. The combined ether phases are washed with water and saturated sodium chloride solution, dried over sodium sulfate and filtered, and the solvent is evaporated off in vacuo. 6.2 g of oil remain and are reacted without further purification.

Trans-4-bromo-5-hydroxy-7-phenylsulfinyl-2,3,4,5-tetrahydro-1-benzoxepin

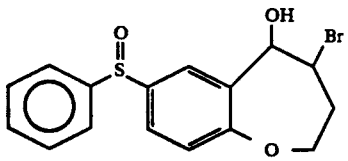

6.20 g of the crude 2,3-dihydro-7-phenylsulfinyl-1-benzoxepin are dissolved in a mixture of 88 ml of DMSO and 8.8 ml of water and cooled to about 10°-12° C. Then, at this temperature, 8.2 g of N-bromosuccinimide are added in one portion while stirring vigorously and keeping the temperature below 25° C. The mixture is stirred at 20° C. for about 1 hour and then stirred into ice-water and extracted several times with ether. The combined ether phases are washed with water and saturated sodium chloride solution and dried over sodium sulfate. The residue after filtration and evaporation of the solvent in vacuo is triturated with methyl tert.-butyl ether and filtered off with suction. White crystals of melting point 147°-149° C. are obtained.

$^1$H NMR (270 MHz/d$^6$-DMSO); δ=7.75–7.67 (m, 3H); δ=7.61–7.46 (m, 4H); δ=7.09 (d, J=8 Hz, 1H); δ=6.12 (d, J=5 Hz, 1H); δ=4.85 (brt, J=5 Hz, 1H); δ=4.51 (m, 1H); δ=4.12 (t, J=4 Hz, 2H); δ=2.78–2.61 (m, 1H); δ=2.19–2.04 (m, 1H).

7-Bromo-5-hydroxy-2,3,4,5-tetrahydro-1-benzoxepin

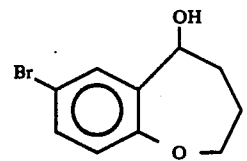

104.9 g (0.64 mole) of 2,3-dihydro-1-benzoxepin-5(4H)-one are dissolved at room temperature in 780 ml of glacial acetic acid and then, while stirring vigorously at 10° C., 113.9 g (0.64 mole) of N-bromosuccinimide are introduced in portions so that the temperature does not exceed 18°-20° C. (about 30 min). The reaction is complete after about 4 hours (TLC check) and the mixture is poured into 3 l of vigorously stirred ice-water and then stirred for 30 minutes. The solid produced which is initially oily crystallizes completely after some time. The solid is filtered off with suction and washed with about 5 l of water. It is dried over calcium chloride in vacuo and crystallized in cyclohexane.

Yield: 117 g, melting point 86°-88° C.

7-Formyl-5-hydroxy-2,3,4,5-tetrahydro-1-benzoxepin

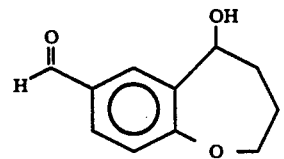

254 ml (0.6 mole) of a 1.7 molar solution of tert.-butyllithium in n-pentane is slowly added dropwise under argon to a stirred solution of 48.6 g (0.2 mole) of 7-bromo-5-hydroxy-2,3,4,5-tetrahydro-1-benzoxepin in 550 ml of absolute THF at −90° C. to −100° C. The mixture is subsequently stirred at −78° C. for 1 hour and then, at this temperature, a solution of 24 ml (0.24 mole) of N-formylmorpholine in 180 ml of absolute THF is added dropwise while stirring vigorously. The mixture is stirred at −78° C. for 1 hour and subsequently allowed to warm to 0° C., and is diluted with diethyl ether and hydrolyzed with ice-water. After extraction several times with diethyl ether, the combined organic extracts are washed with water and saturated brine and dried over sodium sulfate, and the solvent is stripped off in vacuo. 40.7 g of yellowish oil are obtained and reacted further without purification.

7-Cyano-5-hydroxy-2,3,4,5-tetrahydro-1-benzoxepin

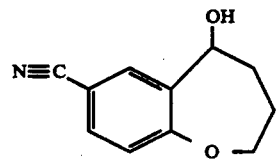

A solution of 27 g of hydroxylamine-O-sulfonic acid in 90 ml of water is added with vigorous stirring to 38 g of the oil isolated above in 210 ml of water at room temperature. The mixture is stirred at room temperature for 0.5 hours and subsequently heated at 60° C. for 1 hour. The mixture is subsequently hydrolyzed with ice-cold 1N-potassium bicarbonate solution and extracted several times with ethyl acetate. The combined organic extracts are washed with water and saturated sodium chloride solution and dried over sodium sulfate, and the solvent is evaporated off in vacuo. The residue is 34 g of yellowish oil which is chromatographed on silica gel (methyl tert.-butyl ether/cyclohexane 1:2). The substance crystallizes on evaporation of the pure fractions. Yield: 19.1 g; Melting point 85°–86.5° C.

7-Cyano-2,3-dihydro-1-benzoxepin

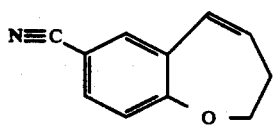

18.9 g (0.1 mole) of 7-cyano-5-hydroxy-2,3,4,5-tetrahydro-1-benzoxepin are heated with 0.3 g of p-toluenesulfonic acid monohydrate in toluene with a water trap for 1.5 hours. After the solution has cooled it is washed with 1N potassium bicarbonate solution, water and saturated sodium chloride solution and, after drying over sodium sulfate, the solvent is evaporated off in vacuo. 16.3 g of solid of melting point 69°–71° C. are obtained.

Trans-4-bromo-7-cyano-5-hydroxy-2,3,4,5-tetrahydro-1-benzoxepin

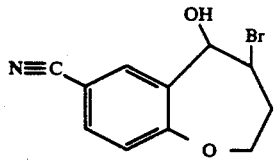

35.5 g (200 mmol) of N-bromosuccinimide are added in one portion to a vigorously stirred solution of 16.25 g (95 mmol) of 7-cyano-2,3-dihydro-1-benzoxepin in 363 ml of dimethyl sulfoxide/water 10:1 at 12°–15° C. The temperature is controlled with a cooling bath in such a way that 30° C. is not exceeded. After the exothermic reaction has ceased, the mixture is stirred at room temperature for 0.5 hours and hydrolyzed with ice/water. It is extracted 3 times with ethyl acetate, and the organic extracts are washed with water and saturated sodium chloride solution and dried over sodium sulfate. The residue after the solvent has been evaporated off in vacuo is stirred with cyclohexane, and the solid is filtered off with suction.

Yield: 22.6 g; Melting point 126°–128° C.

$^1$H NMR (60 MHz/CDCl$_3$): $\delta=7.87$ (d, J=2 Hz, 1H); $\delta=7.58$ (d, d, J$_1$=8 Hz, J$_2$=2 Hz, 1H); $\delta=71$ (d, J=8 Hz, 1H); $\delta=4.95$ (m, 1H); $\delta=4.60–3.83$ (m, 3H); $\delta=3.1–2.0$ (m, 3H).

7-Cyano-4,5-epoxy-2,3,4,5-tetrahydro-1-benzoxepin

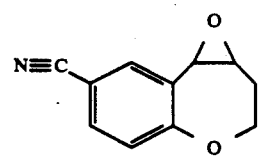

A solution of 22.5 g (84 mmol) of trans-4-bromo-7-cyano-5-hydroxy-2,3,4,5-tetrahydro-1-benzoxepin in 80 ml of DMSO is added dropwise under argon to a stirred suspension of 4.44 g (92.4 mmol) of sodium hydride (55% in oil) in 120 ml of DMSO. The temperature is maintained at 26°–31° C. during this and the mixture is stirred at room temperature for 1 hour. The mixture is hydrolyzed cautiously with ice/water and then stirred for about 20 min, and the precipitated solid is filtered off with suction and thoroughly washed with water. The solid is stirred with cyclohexane, filtered off with suction, thoroughly washed with cyclohexane and dried in vacuo at 60° C.

Yield: 14.1 g of melting point 118°–119° C.

$^1$H NMR (60 MHz/CDCl$_3$): $\delta=7.80$ (d, J=2 Hz, 1H); $\delta=7.53$ (d, d, J$_1$=8 Hz, J$_2$=2 Hz, 1H); $\delta=6.97$ (d, J=8 Hz, 1H); $\delta=4.12$ (m, 2H); $\delta=3.77$ (m, 2H); $\delta=2.55$ (m, 2H).

We claim:

1. A 2,3,4,5-tetrahydro-1-benzoxepin of the formula I

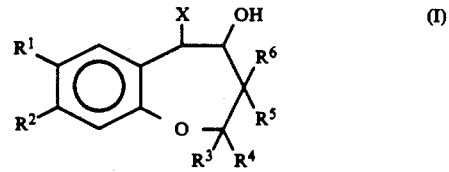

in which

R$^1$ represents H, (C$_1$–C$_4$)-alkyl, OH, (C$_1$–C$_4$)-alkoxy, halogen, CN, NO$_2$, CO-(C$_1$–C$_4$)-alkyl,

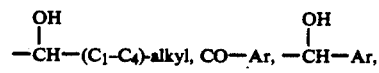

COOH, carboxy-(C$_1$–C$_4$)-alkyl, (C$_1$–C$_4$)-alkyl-SO$_r$— or ArSO$_r$—, where r represents 0, 1 or 2 and Ar represents phenyl, naphthyl or biphenylyl which is unsubstituted or substituted by 1 to 3 identical or different (C$_1$–C$_4$)-alkyl, (C$_1$–C$_4$)-alkoxy, halogen, CN or NO$_2$ radicals, R$^2$ represents H, OH, (C$_1$–C$_4$)-alkoxy or (C$_1$–C$_4$)-alkyl, R$^3$, R$^4$, R$^5$ and R$^6$ are identical or different and represent H or (C$_1$–C$_4$)-alkyl, and X has the meaning of $\alpha$) or $\beta$),

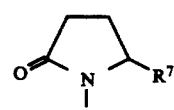

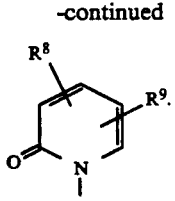

where R⁷ is H or methyl, R⁸ and R⁹ are identical or different and represent H, (C₁-C₂)-alkyl, halogen, nitro or CN.

2. A compound I as claimed in claim 1, wherein R¹ represents H, halogen, CN, nitro, phenylsulfinyl, phenylsulfonyl or benzoyl, with the phenyl radicals in the abovementioned meaning being substituted, and R², R³, R⁴, R⁵, R⁶ and X being as defined in claim 1.

3. A compound I as claimed in claim 1, wherein R¹ represents H, halogen, CN, nitro, phenylsulfinyl, phenylsulfonyl or benzoyl, with the phenyl radicals being unsubstituted or substituted by 1 to 2 identical or different halogen atoms, R² denotes H, and R³, R⁴, R⁵, R⁶ and X are as defined in claim 1.

4. A compound I as claimed in claim 1, wherein R¹ represents H, CN, nitro, phenylsulfinyl, phenylsulfonyl or benzoyl, with the phenyl radicals being unsubstituted or substituted by 1 to 2 identical or different halogen atoms, R², R³, R⁴, R⁵ and R⁶ represent a hydrogen atom and X has the meaning of β with R⁸ and R⁹ assuming the definitions specified in claim 1.

5. A compound I as claimed in claim 1, wherein R¹ represents H, CN, nitro, phenylsulfinyl, phenylsulfonyl or benzoyl, with the phenyl radicals being unsubstituted or substituted by one halogen atom, R², R³, R⁴, R⁵ and R⁶ represent a hydrogen atom and X has the meaning of α with R⁷ being as defined above.

6. A 2,3,4,5-tetrahydro-1-benzoxepin of the formula I

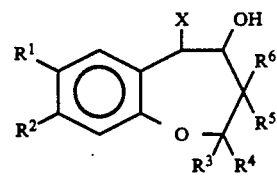

in which
R¹ represents CO—Ar or ArSO$_r$—, where r represents 0, 1 or 2 and Ar represents phenyl,
R² represents H, OH, (C₁-C₄)-alkoxy or (C₁-C₄)-alkyl,
R³, R⁴, R⁵ and R⁶ are identical or different and represent H or (C₁-C₄)-alkyl, and
X has the meaning of α) or β),

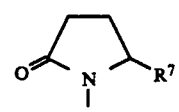

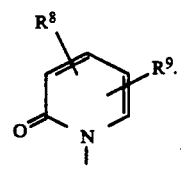

where R⁷ is H or methyl, R⁸ and R⁹ are identical or different and represent H, (C₁-C₂)-alkyl, halogen, nitro or CN.

7. A pharmaceutical composition for the treatment of obstructive airway disorders which comprises an effective amount for said treatment of a compound of the formula I as claimed in claim 1 together with a pharmaceutically acceptable vehicle.

8. A pharmaceutical composition for the treatment of obstructive airway disorders which comprises an effective amount for said treatment of a compound of the formula I as claimed in claim 6 together with a pharmaceutically acceptable vehicle.

9. A method for the treatment of obstructive airway disorders in a mammal which comprises administering to said mammal an effective amount for said treatment of a compound of the formula I as claimed in claim 1.

10. A method for the treatment of obstructive airway disorders in a mammal which comprises administering to said mammal an effective amount for said treatment of a compound of the formula I as claimed in claim 6.

* * * * *